(12) United States Patent
Amir et al.

(10) Patent No.: US 9,335,299 B2
(45) Date of Patent: May 10, 2016

(54) METHOD AND SYSTEM FOR TESTING A BUNDLE OF TUBULAR OBJECTS GUIDED BY A COMPUTING DEVICE

(75) Inventors: Noam Amir, Ness-Ziona (IL); Tal Pechter, Ramat-Hasharon (IL); Oded Barzelay, Sha'arei-Tikva (IL)

(73) Assignee: ACOUSTICEYE LTD, Tel Aviv (IL)

( * ) Notice: Subject to any disclaimer, the term of this patent is extended or adjusted under 35 U.S.C. 154(b) by 1021 days.

(21) Appl. No.: 13/162,578

(22) Filed: Jun. 16, 2011

(65) Prior Publication Data

US 2011/0320139 A1 Dec. 29, 2011

Related U.S. Application Data

(60) Provisional application No. 61/357,538, filed on Jun. 23, 2010.

(51) Int. Cl.
*G01N 29/04* (2006.01)
*G01N 29/07* (2006.01)

(52) U.S. Cl.
CPC ............ *G01N 29/043* (2013.01); *G01N 29/075* (2013.01); *G01N 2291/044* (2013.01); *G01N 2291/2626* (2013.01)

(58) Field of Classification Search
CPC .................................................. G01N 29/043
USPC ........................................................ 702/39
See application file for complete search history.

(56) References Cited

U.S. PATENT DOCUMENTS

| | | | | |
|---|---|---|---|---|
| 4,952,875 A | * | 8/1990 | Adams et al. .................. | 324/220 |
| 5,475,613 A | * | 12/1995 | Itoga .................. | G01N 29/0609 348/135 |
| 5,679,886 A | * | 10/1997 | Houston ......................... | 73/49.1 |
| 7,372,283 B2 | * | 5/2008 | Furukawa et al. ........ | 324/754.22 |
| 7,663,104 B2 | * | 2/2010 | Obuki et al. ................... | 250/311 |
| 2002/0161940 A1 | * | 10/2002 | Eryurek et al. .................. | 710/15 |
| 2003/0098884 A1 | * | 5/2003 | Christensen .................. | 345/781 |
| 2003/0159530 A1 | * | 8/2003 | Haas et al. ...................... | 73/866 |
| 2004/0179021 A1 | * | 9/2004 | Dickinson ..................... | 345/589 |
| 2004/0179024 A1 | * | 9/2004 | Dickinson ..................... | 345/629 |
| 2004/0255678 A1 | * | 12/2004 | Nagashima et al. ............. | 73/620 |
| 2005/0038825 A1 | * | 2/2005 | Tarabzouni et al. ........... | 707/200 |

(Continued)

FOREIGN PATENT DOCUMENTS

WO WO2008148228 * 12/2008

OTHER PUBLICATIONS

Overall view of an oil and gas refinery, pipelines and towers, heavy industry, Image ID: 123207982.*

*Primary Examiner* — Bryan Bui
(74) *Attorney, Agent, or Firm* — Smith Tempel; Gregory Scott Smith

(57) ABSTRACT

Exemplary embodiments of method and system for guiding a tester of a bundle of similar objects are disclosed. The disclosed embodiments may obtain a picture of the bundle of the similar objects. The image may be processed in order to identify the bundle of similar objects to be tested. Then, the system may determine which object of the similar objects to measure and accordingly it may instruct a tester to associate an object-measuring device with the determined object to be measured. Upon receiving a trigger signal issued by the tester, information is collected regarding the test results of the measured object and information on the location of the measured object. Then the process can proceed for additional objects in the bundle.

8 Claims, 7 Drawing Sheets

(56) References Cited

U.S. PATENT DOCUMENTS

| | | | |
|---|---|---|---|
| 2006/0192574 A1* | 8/2006 | Furukawa et al. | 324/750 |
| 2007/0186149 A1* | 8/2007 | Ghantous et al. | 715/502 |
| 2007/0188446 A1* | 8/2007 | Griffin | 345/156 |
| 2008/0167825 A1* | 7/2008 | Tarabzouni et al. | 702/36 |
| 2009/0217770 A1* | 9/2009 | Hoffmann | 73/861 |
| 2010/0250312 A1* | 9/2010 | Tarabzouni et al. | 705/7 |
| 2010/0272240 A1* | 10/2010 | Cochrane | 378/167 |

* cited by examiner

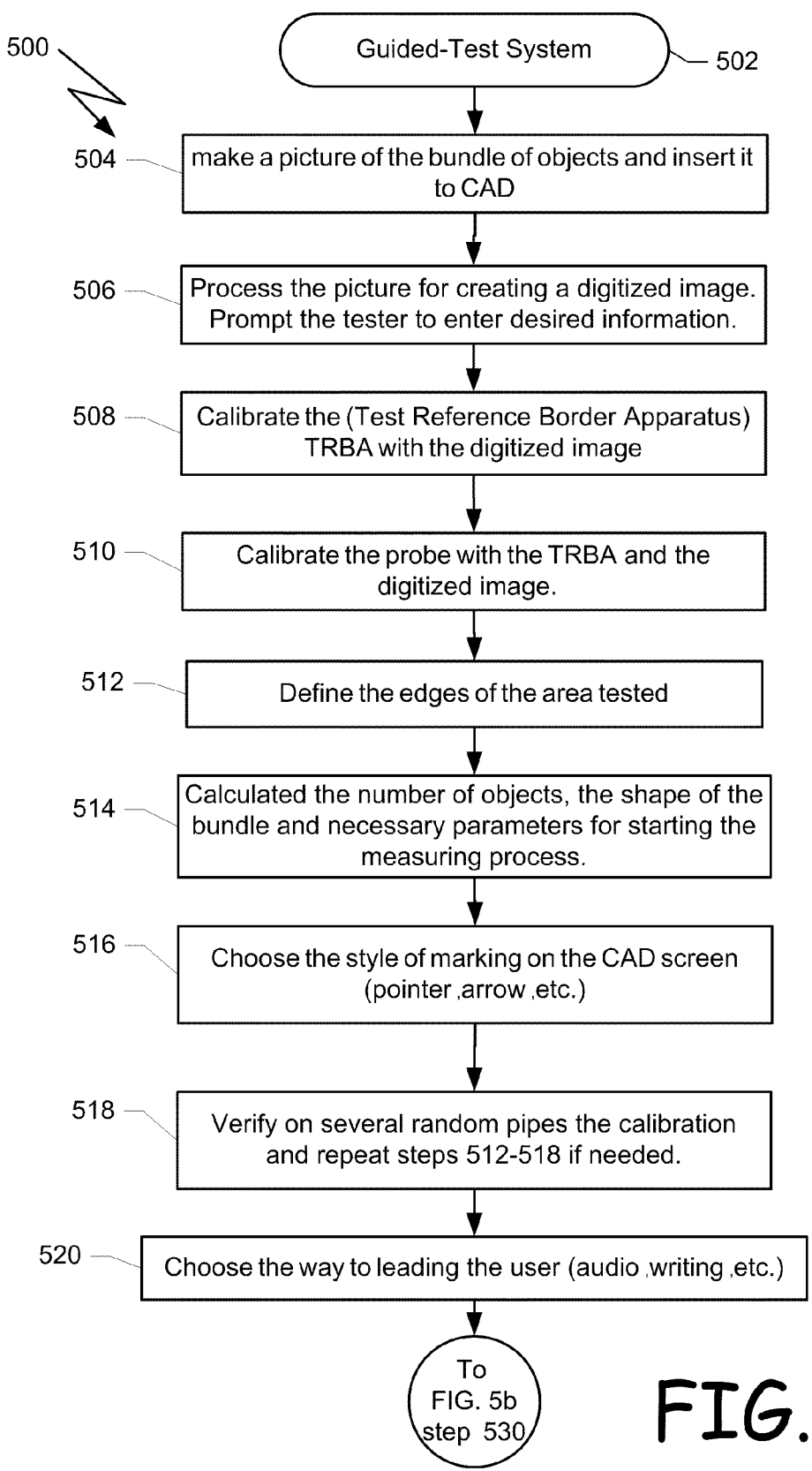

METHOD AND SYSTEM FOR TESTING A BUNDLE OF TUBULAR OBJECTS GUIDED BY A COMPUTING DEVICE

CROSS-REFERENCE TO RELATED APPLICATIONS

This application is a non-provisional application being filed under 35 USC 111 and 37 CFR 1.53(b) and claims the benefit under 35 USC 119(e) of the prior filing date of the United States Provisional Application for patent that was filed on Jun. 23, 2010 and assigned Ser. No. 61/357,538, which provisional is hereby incorporated by reference in its entirety.

BACKGROUND

The present disclosure generally relates to non-destructive testing (NDT) systems, and more particularly, the disclosure relates to a system and method that enable an efficient and rapid testing of a bundle of objects.

Many different systems comprise one or more bundle of objects. Objects such as, but not limited to: tubes (pipes). Exemplary systems comprising a bundle of pipes can be: heat exchangers, reactors, air conditioner systems, manifolds, cooling passageways, power stations, refineries, chemical plants, etc. Fluid or air flowing through the tubes may often leave a gradual accumulation of deposits on the inner surface of the tubes creating constrictions along the tubes (pipe). Alternatively, the flow may create wall-loss such as pitting, erosion, etc., along the tubes.

The different types of defects can degrade the efficiency of the bundle of tubes or developed to leak. Therefore it is common practice to test the inner surface of the tubes periodically. There are a few known methods and systems for examining and evaluating which tubes (pipe) need to be cleaned, replaced, fixed or plugged. Some of the methods and systems use a non-destructive testing (NDT) such as, but not limited to: Acoustic pulse reflectometry (APR), visual methods using boroscopes, methods using eddy current, etc.

Acoustic pulse reflectometry (APR) is a generic name given to a family of systems and methods used to measure an acoustic response of a given system/object. The term APR is derived from the fact that an excitation pulse (input signal) is applied to a system/object being tested, and the reflections (acoustic response) created inside the system/object are measured and analyzed.

Various algorithms are applied to the received and measured acoustic response of a system/object, in order to gain information regarding the system/object being examined. Information such as, but not limited to: the inner structure/geometry of the system under test; unwanted blockage in the system; unwanted holes; wall-loss such as pitting, erosion; internal deformations; etc. and the place of the defect in the system.

A more thorough definition and/or standards on Acoustic pulse reflectometry (APR) can be found at AcousticEye web site: www.acousticeye.com, for example. Additional information regarding APR non-destructive testing system on tubular objects can be found in U.S. patent application Ser. No. 11/996,503 the content of which is incorporate herein by reference.

BRIEF SUMMARY

We found that conducting a manual test on a system that comprises a bundle of objects (tubes, for example) can be complex and prone to human mistakes. Because in some systems the number of objects, which are under test, may be in the range of a few hundred up to a few thousands. An exemplary condenser in a power station may have more than 20,000 pipes (tubes), for example. Additionally the objects under test may be stacked in a bundle, with no specific logic-order or marking.

The objects may be crowded together. For example a diameter of a single pipe (tube) may be 2.5 cm with a pitch of 3.0 cm. And on top of all the above obstacles the objects may be similar in shape and/or color to each other, such that a person cannot be able to tell the difference between them.

The above obstacles may cause one or more human mistakes. Mistakes such as, but not limited to: skipping a pipe, mistakably re-measuring the same pipe, relating a measured result to a wrong object under test, and so on.

FIG. 1A depicts an exemplary portion of a common system 100 that comprise a plurality of bundles 102a-n of objects 104. In FIG. 1A the exemplary objects under test are tubes (pipes) 104. The plurality of tubes (pipes) 104 may be stacked together in a bundle 102. The tubes 104 may be very close to one another, only a few millimeters apart. In an alternate embodiment there may be a different number of tubes 104 in each bundle 102. The size of the tubes and/or bundles may differ from one another.

FIG. 1B depicts another exemplary bundle of pipes (tubes) of a heat exchanger 110, for example. The heat exchanger 110 can comprise a plurality of tubes 112 arranged in a cross shape, for example. FIG. 1A and FIG. 1B are for illustration purposes only and are drawn out-of-scale.

It should be noted that the objects under test may be other than tubes, meaning they are not restricted to tubes (pipes) alone. It should also be noted that the terms "tube", "pipe" and "object" may be used interchangeably herein. Henceforth, the description of the embodiments of the present disclosure may use the term "object" as a representative term for an "object inside a bundle of similar objects".

Bundles of pipes may need to be tested periodically. Furthermore a person conducting the test may be required to record the test results per each object he has tested. The recording is important for different purposes and reasons. One exemplary purpose can be for detecting an object that needs to be cleaned or replaced. An object that needs to be cleaned or replaced and is not detected may cause many problems. Problems such as, but not limited to: higher power consumption; rupture; degrade the overall system performance; etc.

Another exemplary purpose for periodically testing a system can be for creating statistic databases from which a person skilled in the art can conclude which environment condition affect the object state, and/or for monitoring the time affect on the quality of the objects, etc. The database and conclusion can be helpful for troubleshooting and/or maintenance.

Often the testing may require shutting down part of a system under test or shutting down the whole system under test. Shutting down a system for a long period can cause different problems; therefore the testing is required to be conducted as rapidly as possible. For example, if the system is a general heat exchanger in a power stations. The power station manager may put much stress on the tester to test rapidly in order to return to normal condition, before causing great lost in income. We found that the pressure on the tester may lead him to make additional human mistakes.

We also found that in some cases the tester, in advance, may decide not to conduct the test on all the objects. Thus only a sample of the objects is tested. Furthermore in some cases the tester is required to document the results per each object he has tested. The tester is sometimes even required to conduct more than one test per each object. These requirements increase the testing-time. Furthermore, these requirements can cause additional human mistakes. Mistakes such as, but not limited to: mistake in associating the measured report to the correct object, skipping an object by mistake, mistakably re-measuring the same object, and so on.

The above-described deficiencies in measuring bundles of objects do not intend to limit the scope of the inventive concepts in any manner. The deficiencies are merely presented for illustrating an existing situation.

Exemplary embodiments of the present disclosure provide novel system and methods for testing bundles of objects according to a computing-assistance device that can guide the tester to which object to measure; identify which objects were already measured; record measuring results together with the measured object's location information. Thus preventing human mistakes and conducting the test efficiently and rapidly.

It should be noted that the term "computing-assistance device" (CAD) henceforth, the description, drawings and claims of the present disclosure may be used as a representative term for different computing devices such as, but not limited to: personal computer (PC), a notebook computer, a cellular phone, handheld computer, a personal data assistant (PDA), device with wire or wireless communication capabilities, etc.

FIG. 2 schematically illustrates a simplified schematic drawing of relevant elements of an exemplary Guided-Test System (GTS) 200 that can operate according to certain exemplary techniques of the present disclosure. The Guided-Test System (GTS) 200 may comprise a computing-assistance device (CAD) 220. The computing-assistance device 220 can be a computer, for example. In an alternate embodiment the computing-assistance device 220 can be: a PDA, a notebook computer, a cellular phone, handheld computer, and so on. The computing-assistance device (CAD) 220 may comprise different modules. Modules such as, but not limited to one or more of the following elements: a screen, a picture and/or data input slot, an input data receiver, a speaker, and/or an output, etc. Yet, in other exemplary embodiment the CAD 220 can be the computing device that is used by an APR system.

The computing-assistance device (CAD) 220 can receive a picture of the front of a system under test. The system under test can be a plurality of bundles 220a-n of pipes 204, for example. In an alternate embodiment the system under test can be a plurality of bundles of similar objects that are not pipes. Henceforth, the description, drawings, and claims of the present description may use the term "pipes" ("tubes") as a representative term of a "similar objects gathered in a bundle".

The picture can be taken by a tester 240 using a common digital camera, for example. Alternatively the CAD 220 may receive a drawing of the front of the plurality of bundles 220a-n of objects 204 under test; or a scanned drawing; or information from a computer design software regarding the front of the plurality of bundles 220a-n of objects 204 under test; etc. Henceforth, the description, drawings, and claims of the present description may use the term "picture" as a representative term for different options of "entering information regarding the structure of the front of a system under test". The tester 240 may be a human tester. In an alternate embodiment the tester maybe a robot, for example The CAD 220 may present the received picture of the system under test on its screen. The CAD 220 may have image-processing capabilities. Thus the CAD 220 can identify a bundle 202 and can identify a pipe 204, for example. The CAD 220 can further mark and/or index on the displayed picture, on the CAD 220 screen, the detected objects (bundle, pipe, etc).

CAD 220 may further prompt the human tester 240 to deliver information for the image processing. Information such as, but not limited to: the diameter of the pipes 204, the thickness of the pipe's 204 wall, the pitch between pipes 204, etc. CAD 220 can further prompt the tester 240 to mark two pipes 204 along a row of pipes 204 and two pipes 204 along a column of pipes 204. The input from the tester 240 to the prompting requests of the CAD 220 may be used while processing the picture of the bundles into digitized image, for example. In the digitized image each pipe can be given an identification number (ID), for example.

In an exemplary embodiment, the ID of a pipe 204 can reflect a junction of a row of pipes and a column of pipes in which the pipe 204 is located at. CAD 220 may further indicate a few suspected areas in the digitized image in which a human involvement is needed for assisting the automatic process in defining the certain areas in the cross section of the bundles 202a-n, for example. Exemplary suspected areas can be areas that the lightning around them is poor.

An exemplary embodiment of the present disclosure, that comprises the CAD 220 and a picture of the front of the system under test, can lead the human tester 240 to the next pipe 204 to be measured. The CAD 220 may receive the measuring results as input. Upon receiving the results of that measuring, the results can be stored in association with the ID of that pipe 204, for example. Such an embodiment can increase the efficiency of the measuring process, because the human tester 240 will not need to remember and determine which pipe 204 and/or which bundle 202a-n to test next, and to which pipe 204 to associate the measured result, and so on. Because the tester 240 will be assisted by the CAD 220 shown processed picture with markings and/or CAD 220 directions.

GTS 200 may further comprise a Test-reference-border apparatus 210 (TRBA). The TRBA 210 can be placed adjacent to a portion of the system under test. In an alternate embodiment the TRBA 210 can be placed adjacent to the whole system under test. In an alternate embodiment the TRBA 210 can be adjacent to one or more edges of the bundle of the objects that need to be tested, and so on. The TRBA 210 can be adjacent different ways. Exemplary ways can be: placing the TRBA 210 so that it surrounds a portion of the system under test in a wrapping-like way; placing the TRBA 210 next to an edge of the system under test on top of a pole; hang above the bundle under test, etc.

The Test-reference-border apparatus (TRBA) 210 can be of a different shape, material, size, etc. In the exemplary embodiment depicted in FIG. 2 the shape is a rectangle frame (marked in fragmented-line pattern in FIG. 2), but it can be in a different shape (an 'n'-like shape, an 'L'-like shape, a 'T'-like shape, etc.).

The Test-reference-border apparatus (TRBA) 210 may further comprise a plurality of TRBA Modules (TRBAM). Exemplary modules may be: sensors, antennas, transmitters, receivers, encoders, measuring tapes, and so on.

The GTS 200 may further comprise a portable probe 230. The portable probe 230 may be associated to a measuring equipment (ME) (not shown in FIG. 2) used to measure the pipes conditions. In an exemplary embodiment the TRBA 210 may be capable of sensing the position of the portable probe 230. The TRBA 210 may comprise a plurality of sensors that can sense the portable probe 230, and thus can indicate the portable probe's 230 position. In an exemplary embodiment there may be a transmit-receive relation between the TRBAM and the portable probe 230, for example. The TRBAM may comprise a plurality of Radio-Frequency (RF) antennas and receivers, and the portable probe 230 may comprise an RF antenna and transmitter.

In an alternate exemplary embodiment the TRBAM may comprise a plurality of magnetic field creators, and the portable probe 230 may comprise a magnetic element; In yet another exemplary embodiment the TRBAM may comprise a plurality of Ultra-sonic antennas and receivers, and the portable probe 230 may comprise an Ultra-sonic antenna and transmitter; In yet another exemplary embodiment the TRBAM may comprise a plurality of optic sensors and the portable probe 230 may be a light source, such as LED, for example.

In yet another embodiment the above described TRBAM receivers may be transmitters and the above described portable probe's transmitter may be a receiver. In yet another embodiment the receivers can be transceivers (a combination of receiver and transmitter) and the transmitter can be a transceivers.

In an exemplary embodiment the portable probe 230 may be part of the measuring equipment. For example if the measuring equipment is an APR system, such as but not limited to the one disclosed in patent application Ser. No. 11/996,503, then the portable probe 230 can be attached to a hand held unit of the APR measuring equipment, for example.

In an exemplary embodiment a portable probe can be in a cross-shape. In another exemplary embodiment the antennas of the portable probe and the TRBA 210 can be omni directional, while in other embodiments the antennas can be directional, etc. Another exemplary embodiment of the TRBA 210 and the portable probe 230 can be a combination of two or more of the above-described transmitters and sensors, for improving the accuracy of the system.

In an exemplary embodiment the CAD 220 may communicate with the portable probe 230 and/or with the TRBA 210 and/or the TRBAM. The communication can be wired or wireless communication. In an exemplary embodiment when the tester 240 wishes to measure the condition of a certain pipe 204 in a bundle 202a-n, before measuring the tester 240 can signal the CAD 220 that a measurement is about to begin. The tester 240 can signal the CAD 220 by pressing an indicating button (a trigger) on the portable probe 230, for example. Once the CAD 220 receives the signal a procedure for determining/identifying the portable probe's 230 position may begin.

An exemplary method for determining/identifying the portable probes 230 location may be: transmitting a signal via the portable probe 230, and having the CAD 220 analyze the signals received by the different TRBAM of the TRBA 210. The received signals may comprise information from which the portable probe's 230 position can be calculated. Meaning the portable probe 230 can transmit an RF signal, for example. The RF signal can be a frequency in the range of a few MHz or GHz, for example. The plurality of antennas and receivers of the TRBA 210 can receive the RF signal.

Each TRBA's 210 receiver can be associated with an analog phase detector, for example. Each TRBA's 210 receiver can send to the CAD 220 the received signals. CAD 220 may collect, the signal received from the plurality of TRBA's 210 receivers analyze the phase shift between the transmitted signal and each of the received signals. By comparing the phase difference of the received signal from at least two TRBA's 210 antennas CAD 220 can calculate and determine/identify the portable probes 230 position. In some embodiments more then two received signals are processed in order to improve the accuracy of the calculated location or when the surface of the bundle is not flat, for example. In some of those embodiments the wavelength of the RF signal may be longer than the size of the system under test.

Another exemplary method for determining/identifying the portable probes 230 location can be: transmitting a plurality of different signals via the plurality of transmitters and antennas of the TRBA 210 and having the CAD 220 analyze the received different signals by the portable probe 230. The received signals may comprise information from which the portable probe's 230 position can be calculated. The different transmitted signals may comprise: a synchronize section, a time indication, a termination section, a predetermined sequence of bits, etc. Each TRBA 210 transmitter can transmit a signal in a predefined carrier-frequency that will distinguish it from the other transmitters, for example. Each carrier-frequency may carry a predefined data sequence.

The delay in time between the received signals from each transmitting antenna of the TRBA 210 can indicate the distance between the portable probe 230 and each transmitting antenna of the TRBA 210. CAD 220 may process the distance of the portable probe from each transmitting antenna of the TRBA 210 in a sphere-like shape. Wherein the center of each sphere is one of the transmitting antennas and the radios is the calculated distance that is based on the time-delay, for example. CAD 220 may further process the junction/crossing-point of the plurality of spheres, from at least two TRBA's 210 transmitting antenna, for example. The junction/crossing-point of the plurality of spheres can be considered as the location of the portable probe 230. In some embodiments more then two received signals are processed in order to improve the accuracy of the calculated location or when the surface of the bundle is not flat, for example.

In an exemplary embodiment the carrier-frequency of the transmitting signal can be an RF signal in a frequency in the range of few hundreds MHz to few GHz, for example. In another exemplary embodiment the carrier signal can be a Near Infra Red (NIR) light, etc. An RF signal as well as the NIR signal can propagate in the speed of light. Thus a distance of 1 cm can be analogue by a delay of 0.033 nsec between the transmitting time of the signal and the receiving time of the signal, for example.

In other exemplary embodiment, the carrier-frequency of the transmitting signal can be an ultrasonic signal in a frequency range of 100 Khz to 100 MHz for example. In such an embodiment a distance of 1 cm can be analogue by a delay of 33 microsec between the transmitting time of the signal and the receiving time of the signal.

In yet another alternate embodiment the CAD 220 may use two or more following cameras (not shown in the drawings) to follow the portable probe 230. The cross junction between two following-camera tracings of the portable probe 230 may be marked on the displayed picture as the position of the hand held probe, for example.

Yet another exemplary embodiment for determining the location of the portable probe may be implemented by a mechanical positioning detection system. An exemplary embodiment of a mechanical positioning detection system may be attached to the portable probe of the APR system. The portable probe may be attached by via a measuring tape to a pulley. The pulley may comprise a protractor-encoder than can measure the angle of the measuring tape from a vertical from the pulley and a length-encoder that can measure the length of the measuring tape from the pulley to the hand held probe. Such a system may measure the distance and the angle of the portable probe from a vertical line going down from a predefine location. An exemplary predefine location can be the center of the pulley, for example. More information on an exemplary embodiment of a mechanical positioning system is disclosed below in conjunction with FIG. 4.

The CAD 220 may mark the position of the portable probe 230 on the picture displayed on the CAD's 220 screen. In an exemplary embodiment the CAD 220 may mark the portable probe's 230 position each time the tester 240 signals (triggers) the CAD to mark the position. The tester 240 can signal the CAD 220 by pressing a button on the portable probe 230, for example. In an alternate embodiment the portable probe 230 may have an electrical circuit that can be activated each time the portable probe 230 touches an object. For example the electrical circuit may comprise a micro-switch that each time it is pressed against a pipe it activates the electrical circuit, signaling the CAD 220 to mark the position of the object on the displayed picture. An alternate embodiment can have a micro-switch at the edge of the portable probe, and when the portable probe touches an object to be tested the micro-switch is pressed. Furthermore the CAD 220 may further record and mark on the screen the objects that were already tested by the tester.

In the beginning of each test, the tester 240 may conduct a few calibration steps. Exemplary calibration can be: calibrating the portable probe 230, the TRBA 210, and the picture in the CAD 220 system. The calibrations may be done several times during the testing as well.

Furthermore in some exemplary embodiment a feedback may be given to the tester 240 leading him to the position of the next object to be test. In an exemplary embodiment the feedback commands may be given by the CAD 220. The commands from the CAD 220 may be displayed on the CAD's 220 screen (by words; by a pointing arrow, etc). In an alternate embodiment the commands may be given as vocal commands by the CAD 220, using the CAD 220 speakers.

Exemplary commands given by the CAD 220 may be: move left, move down, move at a 45-angle left, etc. In an exemplary embodiment the CAD 220 may receive input regarding the objects size, pitch, number of objects in a line, etc. Thus the CAD 220 may instruct the tester 240 to move in object-steps. Exemplary object-steps may be: move one pipe 204 left. Furthermore the received input regarding the objects size and pitch may be used by the CAD 220 to detect the objects more easily.

CAD 220 may mark the objects with numbers on the screen. In an exemplary embodiment the CAD 220 may further receive the test results for each object been tested from the APR system, for example. The CAD 220 may record the test results along with the position of the object (or the ID of the object, a number that reflects the junction of the relevant column number and row number). At the end of the test the CAD 220 may output a detailed test report. The test report may comprise the measurement results associated to the ID of the pipe and bundle measured. The test report may further comprise a picture of the system under test with the ID marks added to the pipes and bundles. The test report may further comprise graphs of the measurements, and so on. The CAD 220 may further record a plurality of test results (if conducted by the tester) for each object and output them as well.

The automatic recording, by the CAD 220, of the objects that were tested and their test result can save time. Thus the periodic testing can be done more frequently, and by that can prevent damages in the system that utilizes the bundle of pipes. More frequent periodic tests, and recording of them, can help in building a statistic database. The statistic database can help a person skilled in the art to conclude which environment condition affects the object state; schedule preventing maintenance; and so on. The database and conclusion can be very helpful for troubleshooting; planning/re-planning the positioning of the object; etc.

Furthermore since the testing can be done in a more efficiently and rapidly the owner of the system can conduct the test himself. This can reduce maintenance budget, since the down time is reduced.

The foregoing summary is not intended to summarize each potential embodiment or every aspect of the present invention, and other features and advantages of the present invention will become apparent upon reading the following detailed description of the embodiments with the accompanying drawings and appended claims.

Furthermore, although specific exemplary embodiments are described in detail to illustrate the inventive concepts to a person skilled in the art, such embodiments can be modified to various modifications and alternative forms. Accordingly, the figures and written description are not intended to limit the scope of the inventive concepts in any manner.

BRIEF DESCRIPTION OF THE SEVERAL VIEWS OF THE DRAWING

Exemplary embodiments of the present disclosure will be understood and appreciated more fully from the following detailed description, taken in conjunction with the drawings in which:

FIG. 5A and FIG. 5B schematically illustrates a flowchart showing relevant acts of an exemplary method that a GTS may operate, according to exemplary techniques of the present disclosure.

DETAILED DESCRIPTION OF EMBODIMENTS

Turning now to the figures in which like numerals represent like elements throughout the several views, exemplary embodiments of the present disclosure are described. For convenience, only some elements of the same group may be labeled with numerals. The purpose of the drawings is to describe exemplary embodiments and is not for production purpose. Therefore features shown in the figures were chosen only for convenience and clarity of understanding thus the drawings are drawn out-of-scale.

Figure 1A:
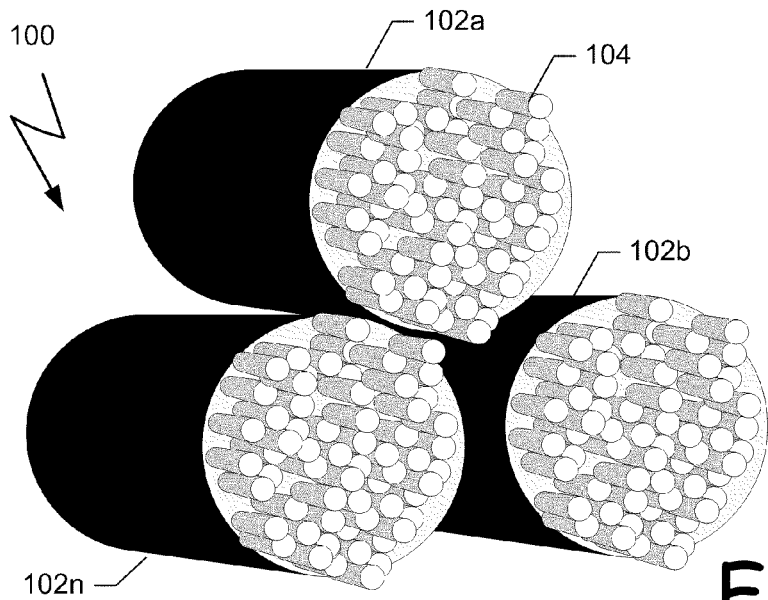
FIG. 1A and FIG. 1B depicts an exemplary portion of a common system that comprise one or more bundles, each bundle comprising a plurality of pipes, in which an exemplary embodiment of the present disclosure may be used.
Figure 1B:
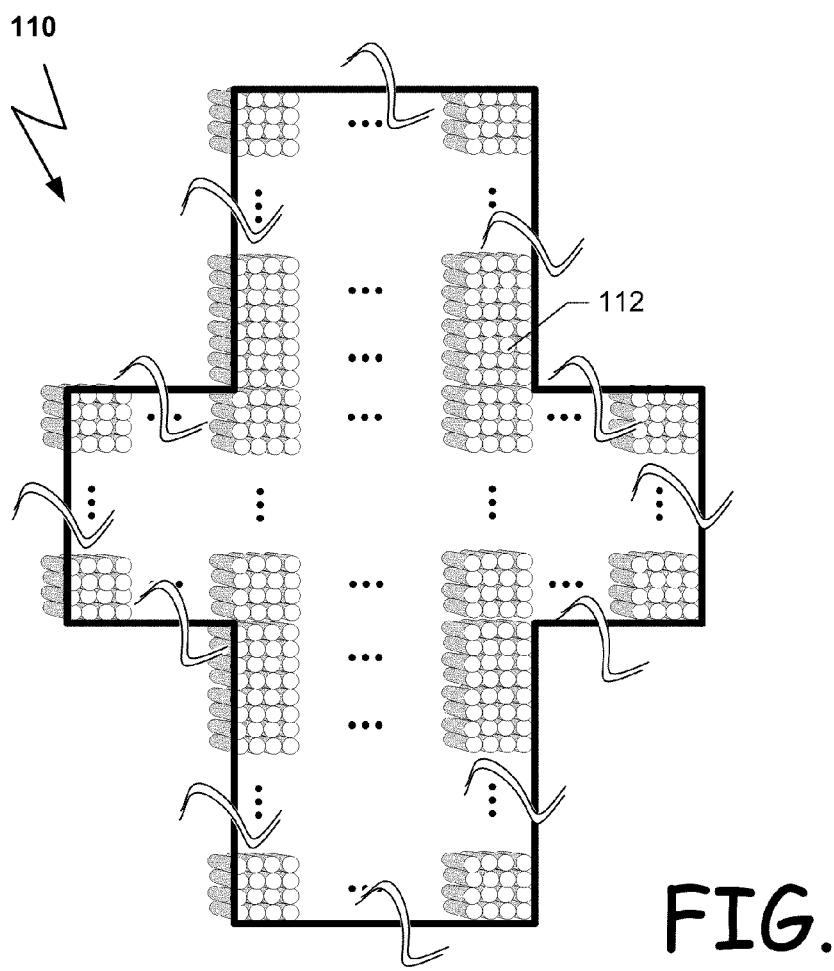
Figure 2:
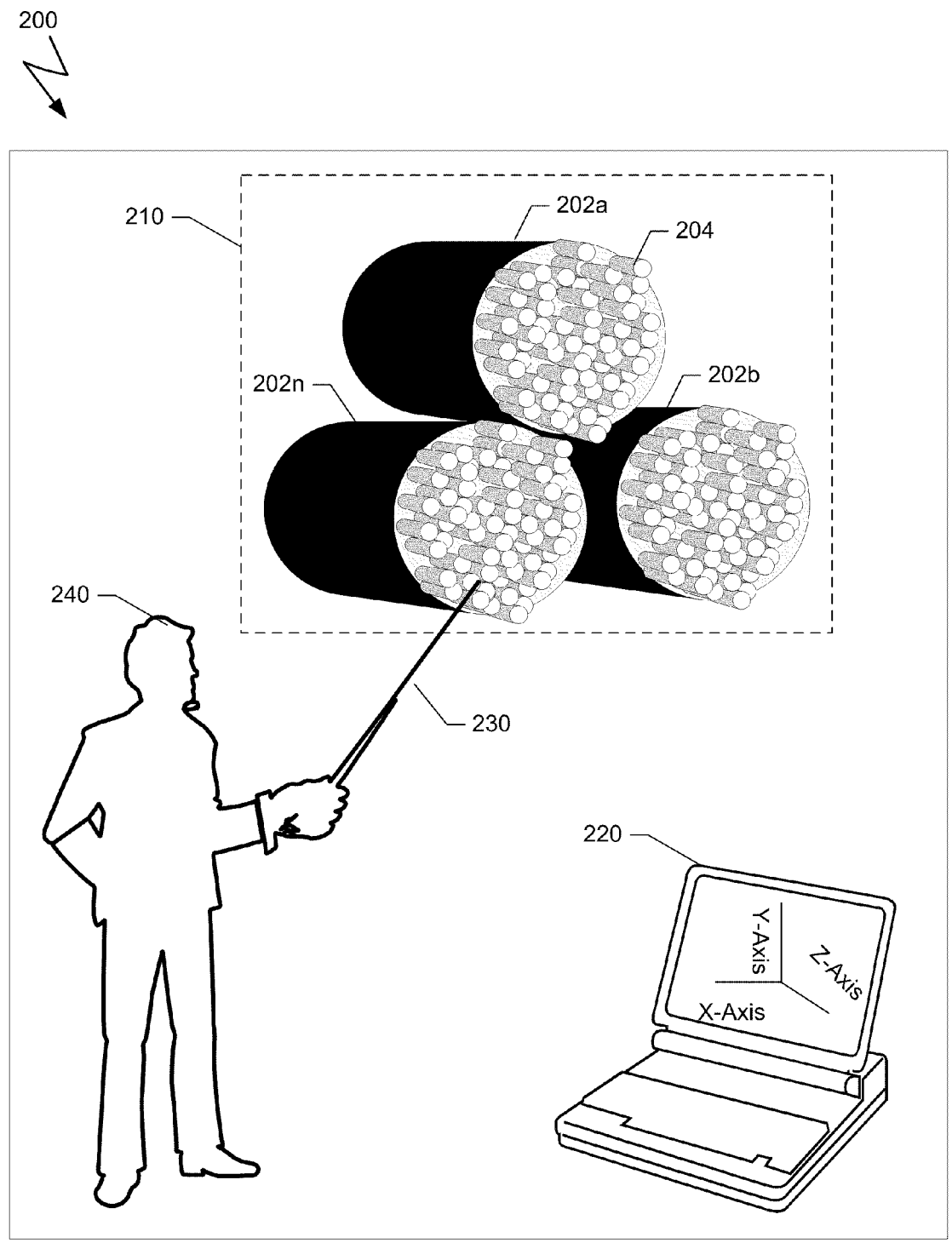
FIG. 2 depicts a simplified block diagram with relevant elements of an exemplary Guided-Test System (GTS) that can operate according to exemplary techniques of the present disclosure.

FIG. 1A, FIG. 1B and FIG. 2 have been described in detailed in the summary above and therefore will not be furthered described.

Figure 3:
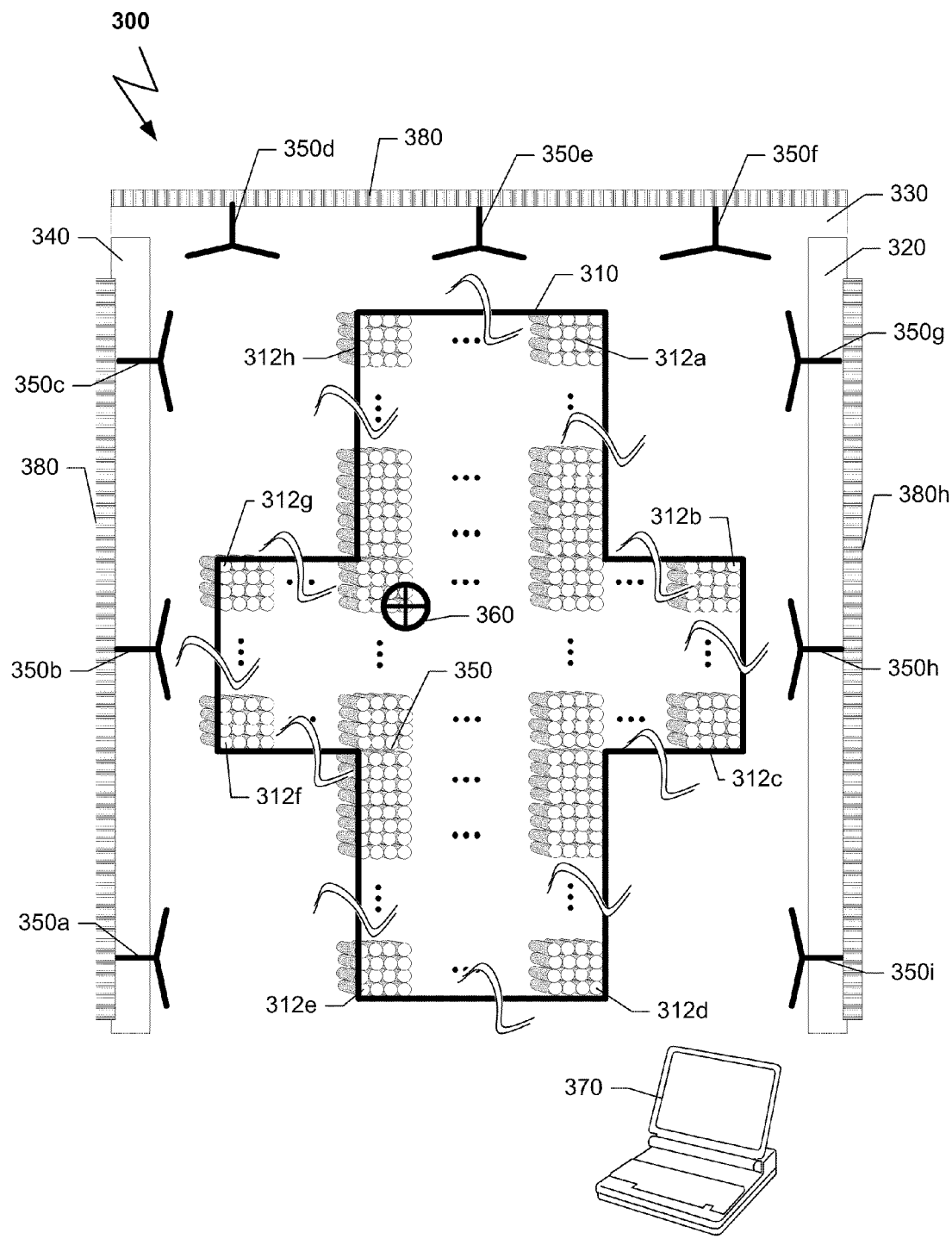
FIG. 3 depicts a simplified block diagram with relevant elements of an exemplary embodiment of a GTS Test-reference-border apparatus that can operate according to exemplary techniques of the present disclosure.

FIG. 3 schematically illustrates a simplified block diagram with relevant elements of an exemplary embodiment of a GTS Test-reference-border apparatus 300 (TRBA) that can operate according to exemplary techniques of the present disclosure. The TRBA 300 may comprise a frame. The frame may comprise a plurality of different parts. Parts such as, but not limited to: poles 320, 330, and 340. In an alternate embodiment the frame may be a one-part frame.

The frame can be of many different shape, size, material, etc. The frame may be adjacent to the system under test. FIG. 3 depicts a frame that surrounds the top and the sides of a system under test. The system under test depicted in FIG. 3 may be a heat exchanger 310, for example. An exemplary embodiment of the heat exchanger 310 may comprise a bundle of pipes 312a-h. The frame may have a plurality of scales 380 on its surface. The TRBA 300 may further comprise a plurality of TRBA Modules 350a-i (TRBAM). Exemplary modules 350a-i may be: sensors, antennas, transmitters, receivers, encoder, and so on. In an exemplary embodiment the TRBAM 350a-i may be similar units. In an alternate embodiment TRBAM 350a-i may be similar but each TRBAM 350a-i may have an additional a unique ID, and so on.

The GTS may further comprise a portable probe 360. The portable probe 360 may be associated to a measuring equipment (not shown in the drawing) used by a tester (not shown in the drawing), for example. The tester can be a human tester or a robot. The portable probe 360 may be associated to the measuring device via a cable, for example. The TRBA 300 may sense the position of the portable probe 360 according to transmit-receive relation between the TRBA Modules (TRBAM) and the portable probe 360, for example. The TRBAM 350a-i may comprise a plurality of sensors that can sense the portable probe 230, and thus can define the position of the portable probe's 360. In one exemplary embodiment the TRBAM 350a-i sensors 350a-i may comprise a plurality of Radio-Frequency (RF) antennas and receivers, and the portable probe 360 may comprise an RF antenna and transmitter.

In an alternate exemplary embodiment the TRBAM 350a-i may comprise a plurality of magnetic field creators, and the portable probe 360 may comprise a magnetic element; In yet another exemplary embodiment the TRBAM 350a-i may comprise a plurality of Ultra-sonic antennas and receivers, and the portable probe 360 may comprise an Ultra-sonic antenna and transmitter; In yet another exemplary embodiment the TRBAM 350a-i may comprise a plurality of optic sensors and the portable probe 360 may be a light source, such as LED, for example.

In yet another embodiment the above described TRBAM 350a-i receivers can be transmitter, and the above described transmitters at the portable probe can be receivers. In yet another embodiment the receivers can be transceivers (a combination of receiver and transmitter) and the transmitter can be a transceivers.

In another exemplary embodiment the antennas of the portable probe and the TRBAM 350a-i may be omni directional, while in other embodiments the antennas may be directional, etc. Another exemplary embodiment of the TRBAM 350a-i and the portable probe 360 can be a combination of two or more of the above-described transmitters and sensors, for improving the accuracy of the system The GTS may further comprise a CAD 370. In an exemplary embodiment when a tester (not shown in FIG. 3) wishes to measure the condition of a certain pipe in the bundle of pipe 312a-h, tester may signal (trigger) to the CAD 370 that a measurement is about to begin. The tester may signal (trigger) the CAD 370 by pressing a button on the portable probe 360, for example. Once the CAD 370 receives the signal a procedure for determining/identifying the portable probe's 360 position may begin.

An exemplary method for determining/identifying the portable probes 360 location may comprise: transmitting a signal via the portable probe 360, and having the CAD 370 analyze the signal received by the different TRBA Modules 350a-i (TRBAM). The received signals may comprise information from which the portable probe's 360 position can be calculated. The portable probe 360 may comprise an RF transmitter that may transmit an RF signal, for example. The RF signal may be a frequency in the range of a few MHz or GHz, for example. The plurality of TRBAM 350a-i may each comprise an antenna and receiver that can receive the RF signal.

Each TRBAM 350a-i receiver may be associated with an analog phase detector, for example. Each TRBAM 350a-i may send to the CAD 370 the received signals. CAD 370 may measure the phase shift of each received signal from the transmitted signal. By comparing the phase difference of the received signals from at least two TRBAM 350a-i CAD 370 can calculate and determine the portable probe's 360 position. In some of those embodiments the wavelength of the RF signal may be longer then the size of the bundle under test.

Another exemplary embodiment and method for determining the portable probe's 360 location the TRBAM 350a-i may include transmitters with antennas, and the portable probe 360 may comprise a receiver with an antenna. The TRBAM 350a-i may transmit a plurality of different signals via the plurality of transmitters and antennas. The portable probe 360 may send the received signals to the CAD 370. The CAD 370 may analyze the received different signals by the portable probe 360.

The received signals may comprise information from which the portable probe's 360 position can be calculated. The different transmitted signals may comprise: a synchronize section, a time indication, a termination section, a predetermined sequence of bits, etc. Each sensor's 350a-i transmitter can transmit a signal in a predefined carrier-frequency that will distinguish it from the other transmitters, for example. Each carrier-frequency may carry a predefined data sequence.

A time-delay between the transmitting command and the received signals from at least two transmitting antenna of the TRBAM 350a-i indicates the distance between the portable probe 360 and the at least two transmitting antenna of the TRBAM 350a-i. CAD 370 can calculate the distance of the portable probe 360 from the transmitting antenna of the TRBAM 350a-i in a sphere-like shape. Wherein the center of each sphere is one of the transmitting antennas and the radios is the calculated distance that is based on the time-delay, for example. CAD 370 may further process the junction/crossing-point of the plurality of spheres, for example. The junction/crossing-point of the plurality of spheres can be considered as the location of the portable probe 360.

In an exemplary embodiment the carrier-frequency of the transmitting signal may be an RF signal in a frequency in the range of few hundreds MHz to few GHz, for example.

In another exemplary embodiment the carrier signal can be a Near Infra Red (NIR) light, etc. An RF signal as well as the NIR signal can propagate in the speed of light. Thus 0.033 nsec delay between the transmitting time of the signal and the receiving time of the signal can be analogue to a distance of 1 cm between the transmitting antenna and the receiving antenna, for example.

In other exemplary embodiment, the carrier-frequency of the transmitting signal can be an ultrasonic signal in a frequency range of 100 Khz to 100 MHz for example. In such an embodiment a delay of 33 microsec between the transmitting time of the signal and the receiving time of the signal can reflects a distance of 1 cm between the transmitting antenna and the receiving antenna.

Figure 4:
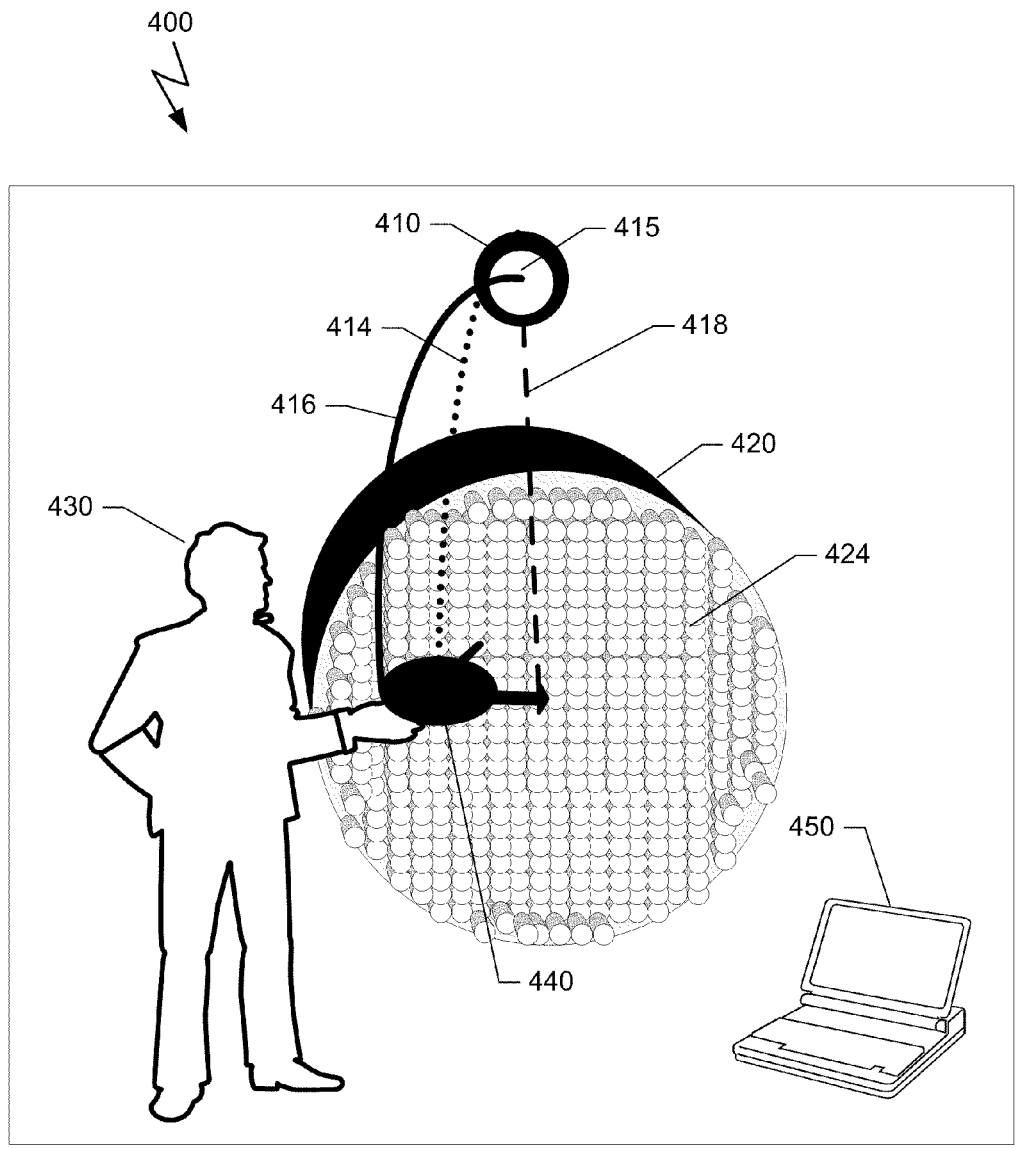
FIG. 4 depicts a simplified block diagram with relevant elements of an exemplary embodiment of a GTS mechanical positioning detection system that can operate according to exemplary techniques of the present disclosure.

FIG. 4 schematically illustrates a simplified block diagram with relevant elements of an exemplary embodiment of a GTS 400 having a mechanical positioning detection system (MPDS), which operates according to certain exemplary techniques of the present disclosure. The GTS 400 may comprise: a pulley 410; a supporting rope 414 for carrying the weight of an APR measuring probe 440; a communication link 416 for connecting the measuring probe 440 with a CAD system 450. Communication link 416 can use wire or wireless technique. In an exemplary embodiment the pulley 410 may be attached to one of the edges of a bundle of pipes under test 420. The pulley 410 may include an internal spool of rope 414 with a return spring keeping the rope 414 tightly for supporting the weight of the APR measuring probe 440. Rope 414 helps a tester 430 in moving the APR measuring probe 440 from one pipe to the other and in holding the APR measuring probe while running the test in a current selected pipe.

A measuring tape 418 can be taut between a mechanical positioning detection system (MPDS) 415 and an adaptor at the edge of the APR measuring probe 440 that is attached to a pipe 424 from the bundle 420. The MPDS 415 can be associated with the pulley 410. The MPDS 415 can comprise an internal spool of measuring tape 418 with a return spring keeping the measuring tape 418 tight for indicating the distance between the MPDS 415 and the measuring probe 440. MPDS 415 may comprise a protractor-encoder that can measure the angle of the measuring tape 418 from a vertical line going down from the MPDS 415. In addition MPDS 415 can comprise a length-encoder that can measure the length of the measuring tape 418 that is rolled out of the MPDS 415. The protractor-encoder and the length-encoder may be associated to a transceiver (not shown in the drawing), for example. The CAD 450 may also be associated to a matching transceiver (not shown in the drawing). The protractor-encoder may send measured angle toward the CAD 450 via the transceiver, for example. The length-encoder may send measured length toward the CAD 450 via the transceiver, for example.

Before starting the monitoring process of the bundle 420, tester 430 may initiate a setup process for calibrating the MPDS 415 with the bundle under test 420. The calibration may comprise entering a picture of the bundle 420 under test into the CAD 450. Furthermore different information regarding the bundle 420 under test may be input by the tester 430 to the CAD 450. Information such as, but not limited to: the diameter, the shape, the pitch of the objects been tested. Coordination between the CAD 450 the protractor-encoder, and the length-encoder may be performed during calibration as well.

During calibration CAD 450 may instruct the tester 430 to move the probe 440 to different pipes in the bundle, for example. Exemplary different pipes can be pipes that will be considered as the edges of the bundle, for example. In an exemplary embodiment the instructions may be given by marking the selected pipes on the picture. The marking may be displayed on the CAD's 450 screen by an arrow pointing on the selected pipe on the displayed picture, for example. In an alternate embodiment the instructions may be given as commands such as, but not limited to: move to the top left; move to the bottom right, and so on. The commands may be written on the CAD's 450 screen, or displayed as writing on the CAD's 450 screen. The location coordinates can be defined by the measured angle from the vertical line and the length of the measuring tape 418.

CAD 450 may process the receiving location coordinates of the selected pipes and the information entered by the tester about the dimension of the bundle and the pipes. The process information can be used in order to adjust the MPDS 415 with the picture of the bundle. After adjusting the MPDS 415 and the picture a validation process can be initiated in which the tester can be instructed by CAD 450 to place the APR measuring probe 440 at a certain pipe and to trigger the MPDS 415 to define/mark, the pipe in the picture over the screen of CAD 450. If the marked pipe is the correct one then the calibration process can be terminated and APR measuring of the pipes can be initiated, if not the calibration process can start from the beginning.

Information from the protractor-encoder and from the length-encoder may be sent toward the CAD 450. The information may be sent by wireless or wired communication. Exemplary information can be: the angle of the measuring tape 418 from the vertical line; the length of the measuring tape 418 from the MPDS 415. This information can be converted to pipes units by using the diameter and the pitch of the pipes. During the APR test the CAD 450 may instruct the tester 430 which pipe 424 to measure next. The instructions may be: move one pipe left; move X pipes left and then Y pipes up from the current pipe; and so on. More information regarding the test and the calibration procedures and methods is disclosed in conjunction with FIG. 5 and FIG. 6.

Figure 5B:
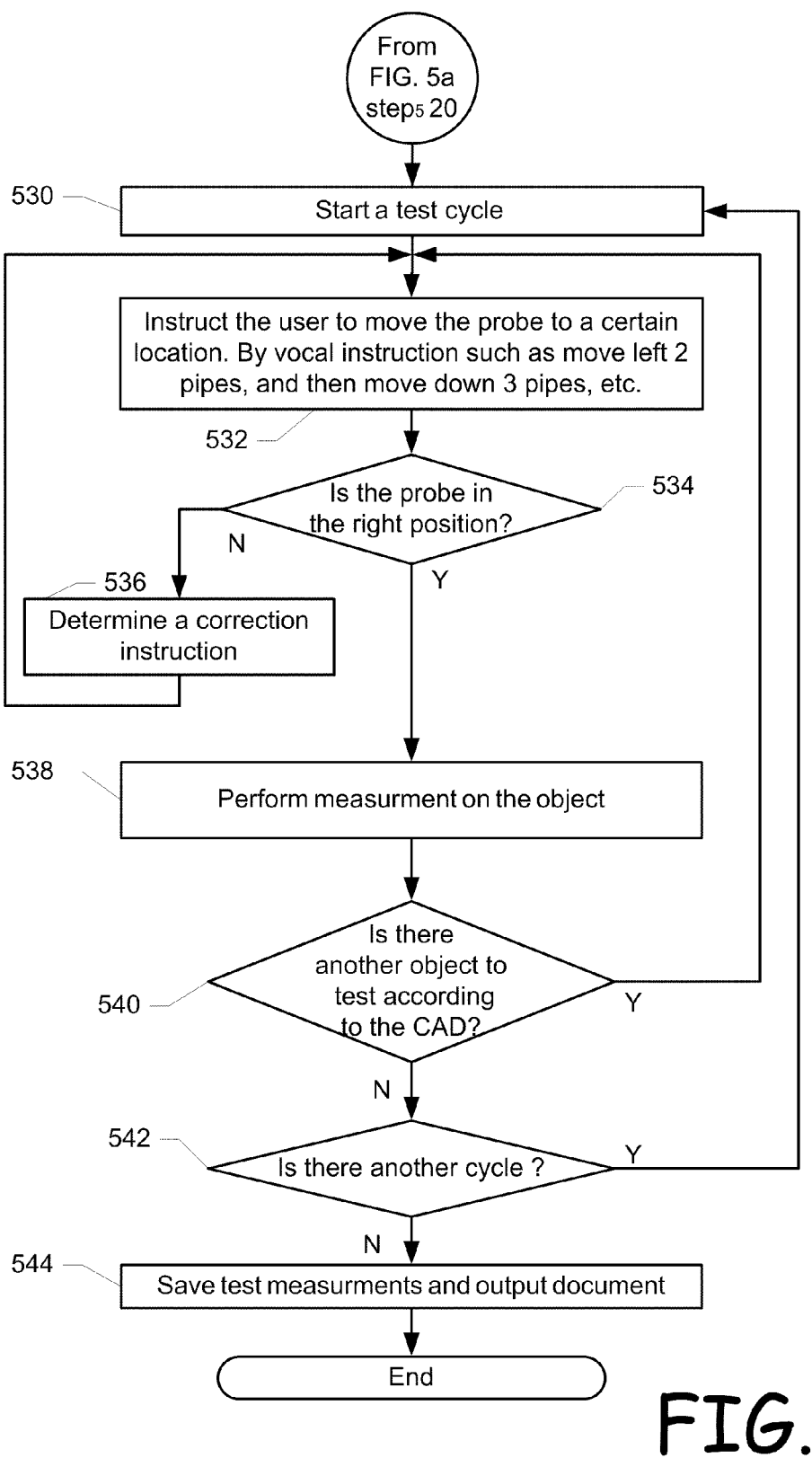

FIG. 5A and FIG. 5B schematically illustrates a flowchart showing relevant processes of an exemplary method 500 that a Guided-Test System may operate accordingly. At act 504 a request for a picture of the bundle of objects may be requested. The picture may be data from a computer-design software, a drawing, a scanned data a photo image, etc. The picture may be sent/inserted to the CAD. Next CAD may process 506 the received picture. A digitized image of the picture may be created 506. The tester may be prompted 506 to enter different information regarding the picture. Information such as the diameter of a pipe, the pitch between pipes, number of pipes in a row or column, etc.

The Test-Reference-Border Apparatus (TRBA) may be calibrated 508 and coordinated 508 with the digitized image. The portable probe may also be calibrated 510 and coordinated 510 with the TRBA and with the digitized image. The calibration process was disclosed above in conjunction with FIG. 3 and FIG. 4.

The edges of the bundle under test may be defined 512. A calculation 514 of the number of objects to be measured may be made. The calculation 514 of the number of objects may be made by the CAD according to information regarding the size, shape, and pitch of the objects, for example. The information regarding the size, shape, and pitch of the objects may be inserted by the human tester, for example. A decision 516 regarding the manner of marking on the CAD screen may be chosen. Exemplary manners can be: an arrow pointing on the displayed picture, to the next object to be measured; a color marking the objects measured on the displayed picture; and so on.

A verifying procedure regarding the calibration may be made 518. The verification 518 may be performed on a few pipes. Exemplary verification may be: the tester may place the portable probe at a certain pipe and check if the marker on the CAD marks the right pipe on the picture, for example. If not fine-tuning may be preformed. Fine tuning can be done by repeating acts 512-518, for example.

Next a decision regarding the manner that the CAD will lead the tester may be made 520. The leading may be by vocal instructions using the CAD's speakers, for example. An alternate embodiment may be by signaling/marking on the displayed picture which pipe to test, and so on.

After the system has been calibrated and coordinated method 500 may proceed to act 530 at FIG. 5B. At FIG. 5B an ARP measurement may be initiated 530. A measurement cycle may begin 530. The tester may be instructed 532 to move the APR portable, toward a certain location/pipe. The location may be the next pipe to be measured, for example. The instruction may be given 532 in the manner chosen at act 520, for example. Exemplary leading instructions may be: move 2 pipes up and 3 pipes left.

Next a decision needs to be made 534, whether the APR portable probe is in the right position. The decision may be made according to the calculated the position of the portable probe by processing information received from the TRBA or the mechanical positioning detection system (MPDS). In an alternate embodiment the tester may verify that the placement is similar to the requested position. If yes 534, then method 500 can proceed to act 538. If not 534, then method 500 may determine 536 an improved instruction, and method 500 can return to act 532.

At act 538 an APR test measurement on the pipe may be executed 538. The measured results may be forward toward the CAD. The measurement results may be stored in association with information on the pipe location or ID. Next a decision needs to be made 540, whether another pipe needs to be tested. CAD may determine if there is another pipe to be tested, for example. If yes 540, then method 500 can return to act 532. If not 540, then method 500 can proceed to act 542.

At act 542 a decision needs to be made whether a next cycle of measurements should be. In an exemplary embodiment CAD may decide if another cycle is needed. In an alternate exemplary embodiment the tester may determine if another cycle is needed. If 542 yes, then method 500 can return to act 530. If 542 not, then the test measurement results can be stored. The test measurements results can be stored 544 in one of the CAD's permanent memories for example. A document with the test measurement results associated with the relevant pipes and information on the location of each measured pipe may be output 544 and method 500 can end.

Figure 6:
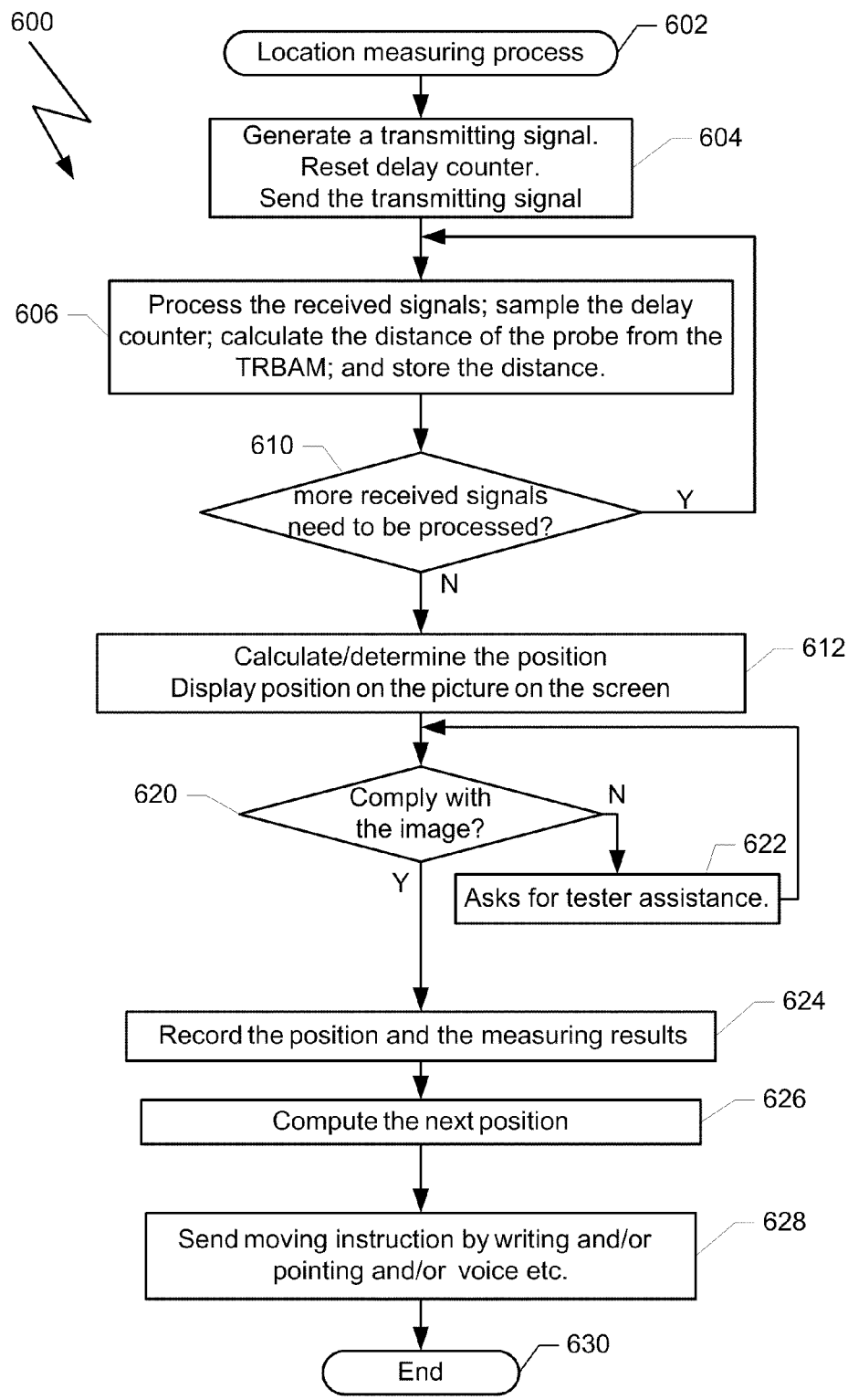
FIG. 6 schematically illustrates a flowchart showing relevant acts of an exemplary method for determining a location of a portable probe, according to exemplary techniques of the present disclosure.

FIG. 6 schematically illustrates a flowchart showing relevant processes of an exemplary method 600. Method 600 may be implemented in a GTS having an TRBA as the one that is illustrated in FIG. 3, for example. Method 600 can be initiated when an APR portable probe's current location is engaged with the current required pipe, for example. Method 602 may be triggered by a signaling given by the portable probe while it is pressed against a pipe currently under test, for example. One or more delay counters may be reset 604. A transmitting signal may be generated and sent at act 604. The transmitting signal may include: synchronization information, time indication, termination sections, etc. In an exemplary embodiment the portable probe may be the one to transmit 604 the generated signal. In an alternate embodiment the TRBAM (TRBA Modules) may be the ones to transmit 604 the generated signal.

The received one or more signals may be processed 606. In an exemplary embodiment the signal may be received 606 by the one or more TRBAM. In an alternate embodiment the signals may be received 606 by the portable probe. The one or more delay counters may be sampled 606. A distance of the portable probe from the one or more TRBAM may be calculated 606 as a function of the time delay between the transmitting and the receiving signals. The calculated distances may be stored 606 in the CAD, for example.

Next a decision needs to be made, whether more received signals need to be processed 610. If yes then method 600 may return to act 606. IF 610 not, then method 600 may proceed to act 612. At act 612 the position of the portable probe may be calculated 612 according to the saved data from the processed received signals. Exemplary method for determining the position of the portable probe may comprise: creating a virtual sphere around at least two TRBAM in a radios similar to the calculated distance of the TRBAM to the portable probe. The crossing point of the spheres may be considered the position of the portable probe. The calculated/identified position of the portable probe may be displayed and/or marked 612 on the picture displayed over the CAD screen, for example.

Next a decision needs to be made, whether the marked position of the portable probe on the picture comply 620 with the portable probe's placement in reality. If 620 not, then method 600 may request 622 assistance from the tester. If 620 yes, then method 600 may proceed to act 624. At act 624 the position of the portable probe may be recorded 624 and saved 624. The APR measurement results of the pipe that the portable probe is engaged with may be recorded 624 and saved 624 as well.

Next method 600 may compute 624 the next object/pipe to be tested and its position. Leading instructions to the next object to be tested may be given 600 and method 600 can end. Exemplary leading instruction may be: move one pipe left and two down; etc. The instructions may be given as vocal instruction using the CAD speakers, for example. In an alternate embodiment they can be displayed over the CAD screen, etc.

In the description and claims of the present disclosure, each of the verbs, "comprise", "include" and "have", and conjugates thereof, are used to indicate that the object or objects of the verb are not necessarily a complete listing of members, components, elements, or parts of the subject or subjects of the verb.

In this disclosure the words "unit" and "module" are used interchangeably. Anything designated as a unit or module may be a stand-alone unit or a specialized module. A unit or a module may be modular or have modular aspects allowing it to be easily removed and replaced with another similar unit or module. Each unit or module may be any one of, or any combination of, software, hardware, and/or firmware. Software of a logical module can be embodied on a computer readable medium such as a read/write hard disc, CDROM, Flash memory, ROM, etc. In order to execute a certain task a software program can be loaded to an appropriate processor as needed.

The present disclosure has been described using detailed descriptions of embodiments thereof that are provided by way of example and are not intended to limit the scope of the invention. The described embodiments comprise different features, not all of which are required in all embodiments of the invention. Some embodiments of the present disclosure utilize only some of the features or possible combinations of the features. Many other ramification and variations are possible within the teaching of the embodiments comprising different combinations of features noted in the described embodiments.

It will be appreciated by persons skilled in the art that the present invention is not limited by what has been particularly shown and described herein above. Rather the scope of the invention is defined by the claims that follow.

What is claimed is:

1. A system that guides a tester while measuring a plurality of similar pipes that are bundled together, comprising:
   a pipe-measuring device;
   a location measuring system associated with the pipe-measuring device and is configured to deliver location information about the location in the bundle of a pipe that is currently measured by the pipe-measuring device;
   a computing-assistance device (CAD) that is configured to:
      obtain information on a front of a plurality of similar pipes that are bundled together;
      obtain location information from the location measuring system about the location of the front of the pipe that is currently measured within the front of the bundle of similar pipes; and
      obtain measurements signals from the pipe-measuring device,
   wherein the measurements signals reflect the condition of the pipe that is currently measured; and
   wherein the location information of the pipe that is currently measured is related to the front of the plurality of similar pipes.

2. The system of claim 1, wherein the computing-assistance device is further configured to report on the condition of the pipe and associate the report with the location of the pipe in the bundle.

3. The system of claim 2, wherein the CAD that is further configured to:
   instruct a tester to associate the pipe-measuring device to a requested-next pipe;
   obtain location information from the location measuring system about the location in the bundle of an actual-next pipe that is currently measured;
   obtain measurements signals from the pipe-measuring device, wherein the measurements signals reflect the condition of the actual-next pipe that is currently measured; and
   report on the condition of the actual-next pipe and associate the report with the location of the actual-next pipe in the bundle.

4. The system of claim 3, wherein the CAD further configured to:
   determine based on the location of the actual-next pipe whether the actual-next pipe is the requested-next pipe if not then correction instruction are given to the tester to associate the pipe-measuring device with the requested-next pipe; if the actual-next pipe is the requested-next pipe then the CAD continues measuring a plurality of pipes from the bundle and creating a report per each pipe.

5. The system of claim 1, wherein the pipe-measuring device is a hand-held probe of an Acoustic pulse reflectometry (APR) system.

6. The system of claim 1, wherein the location measuring system uses transmitting-receiving relation.

7. The system of claim 1, wherein the location measuring system uses a mechanical-position-detection system.

8. The system of claim 1, wherein information on a bundle of similar pipes is obtained from a picture of the bundle.

* * * * *